United States Patent [19]

Briner et al.

[11] Patent Number: 4,607,128

[45] Date of Patent: Aug. 19, 1986

[54] NOVEL SUBSTITUTED PHENYL ETHERS, PROCESS FOR THEIR PREPARATION, AND THEIR USE IN THE PREPARATION OF SUBSTITUTED PHENOLS

[75] Inventors: Paul H. Briner, Faversham; Ronald F. Mason, Ashford, both of England

[73] Assignee: Shell Oil Company, Houston, Tex.

[21] Appl. No.: 817,191

[22] Filed: Jan. 8, 1986

[30] Foreign Application Priority Data

Jan. 9, 1985 [GB] United Kingdom ............... 8500482

[51] Int. Cl.⁴ ..................... C07C 41/16; C07C 29/09; C07C 43/205
[52] U.S. Cl. .................................. 568/655; 568/656; 568/775
[58] Field of Search ....................... 568/655, 656, 775

[56] References Cited

PUBLICATIONS

McBee et al., Jour. Amer. Chem. Soc., vol. 73 (1951) 2375-2376.

*Primary Examiner*—Bernard Helfin

[57] ABSTRACT

Novel compounds of the general formula

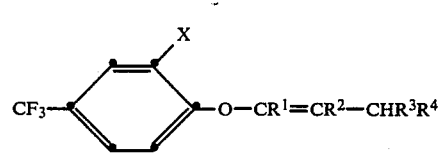

in which X is hydrogen or chlorine, and each of $R^1$, $R^2$, $R^3$ and $R^4$ independently is hydrogen, methyl or ethyl, are useful intermediates in the preparation of the corresponding phenols. They may be prepared by treating a compound of the formula

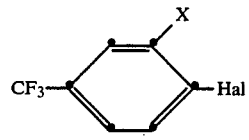

in which Hal is chlorine or fluorine, with a compound of the formula

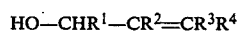

in the presence of a base.

7 Claims, No Drawings

NOVEL SUBSTITUTED PHENYL ETHERS, PROCESS FOR THEIR PREPARATION, AND THEIR USE IN THE PREPARATION OF SUBSTITUTED PHENOLS

BACKGROUND OF THE INVENTION

4-Trifluoromethylphenol and 2-chloro-4-trifluoromethylphenol are useful intermediates in the preparation of certain substituted phenyl ethers—see for example U.S. Pat. Nos. 3,819,755 and 3,888,932. However, these phenols are rather difficult to synthesise, as the trifluoromethyl group tends to be unstable under a wide range of reaction conditions that might normally be used to introduce a hydroxy group onto a phenyl ring. Accordingly much research has been devoted to the preparation of these compounds, and many possible routes have been described—see for example French Specification No. 1,469,596 and German Pat. No. 1,257,784. All such processes, however, are either chemically or economically unattractive.

Applicants have now found a reaction which unexpectedly gives a novel intermediate that can be used in the preparation of these substituted phenols.

DESCRIPTION OF THE INVENTION

This invention provides a compound of the formula

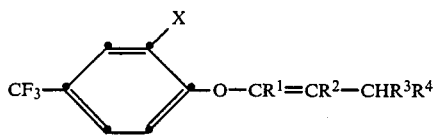

(I)

in which X is hydrogen or chlorine, and each of $R^1$, $R^2$, $R^3$ and $R^4$ independently is hydrogen, methyl or ethyl.

Preferably X is hydrogen, and preferably each of $R^1$, $R^2$, $R^3$ and $R^4$ is hydrogen.

The invention also provides a process for the preparation of a compound of Formula I, that comprises treating a compund of the formula

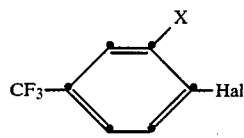

(II)

in which Hal represents chlorine or fluorine, with a compound of the formula $$HO-CHR^1-CR^2=CR^3R^4$$

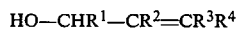

in the presence of a base.

Suitable bases include alkoxides such as sodium or potassium tertiary butoxide; alkali metal, alkaline earth metal and quaternary ammonium hydroxides such as sodium or potassium hydroxide; and alkali metal hydrides and amides. The reaction is preferably carried out in the presence of suitable polar aprotic solvent, for example dimethyl sulphoxide, sulpholane, a polyether such as dimethoxyethane or the various oligo ethylene glycol bis ethers such as bis(2-methoxyethyl) ether (diglyme) or tetraethylene glycol dimethyl ether (tetraglyme) or an amide such as dimethylformamide, dimethylacetamide, hexamethylphosphoramide or N-methylpyrrolidone. Mixtures of solvents may be useful.

The treatment preferably is carried out at a temperature in the range of 70°–200° C., especially 100°–150° C. The molar ratio of the reactants is not crucial; typically the molar ratio of the compound of Formula II to the compound of Formula III is in the range of 1:5 to 5:1, preferably 1:3 to 1:1.

It is most surprising that the process according to the present invention leads to a compound of Formula I. It would have been expected that, on the contrary, the isomeric compound containing the group $$-O-CHR^1-CR^2=CR^3R^4$$

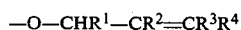

would have been the product prepared by the process of the present invention. Unlike this isomeric compound, which would be expected to be stable under acid conditions, the compound of Formula I can be cleaved using water or an alcohol under acid conditions to produce the corresponding phenol. Accordingly the present invention also provides a process for the preparation of a compound of the formula

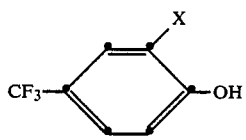

(IV)

that comprises treating a compound of Formula I with water or an alcohol under acid conditions.

The compound used for the cleavage may be water or a mono- or poly-functional alcohol, for example a sugar, for example galactose or glucose, or an alcohol derived from an alkane having up to 8 carbon atoms, for example ethylene glycol, glycerol, trimethylolethane, trimethylolpropane, pentaerythritol, and monoalkanols having up to 4 carbon atoms.

The water or alcohol itself may act as solvent for the reaction, or one or more additional solvents may also be used. Suitable additional solvents include for example hydrocarbons or chlorinated hydrocarbons such as carbon tetrachloride, benzene, toluene or petrol, ketones such as methyl ethyl ketone or acetone, or ethers such as dimethoxyethane, bis(2-methoxyethyl) ether or tetrahydrofuran. The acid used is not critical; mineral acids such as sulphuric, hydrochloric or phosphoric acid, organic acids such as p-toluene sulphonic acid, and solid ion-exchange resins, may all be used. The reaction temperature may vary over a wide range, but is preferably in the range of from 0°–100° C.

If it is desired to prepare a phenol of Formula IV in which X is chlorine, this may be done by using as starting material a compound of Formula I in which X is chlorine. Alternatively, the compound may be prepared by chlorination of the phenol of Formula IV in which X is hydrogen. This reaction may be carried out using any suitable chlorinating agent, for example N-chlorosuccinimide or elemental chlorine, preferably at a temperature in the range of from 0°–150° C., conveniently under reflux or at room temperature. Any suitable solvent may be used, for example a hydrocarbon or chlorinated hydrocarbon such as those listed above.

Surprisingly, it has been found that the compound of Formula IV in which X is chlorine can be obtained easily and in high yield and high purity, if the cleavage of the compound of Formula I (X=H) is carried out in the presence of an inert organic solvent, preferably a hydrocarbon or a chlorinated hydrocarbon, and in the additional presence of a polyfunctional organic alcohol containing at least two hydroxyl groups, and the resulting reaction mixture is chlorinated in situ using elemental chlorine. Typical alcohols which may be present are sugars, for example galactose or glucose, and alcohols derived from alkanes having up to 8 carbon atoms, for example ethylene glycol, glycerol, trimethylolethane, trimethylolpropane and, especially, pentaerythritol.

The following Examples illustrate the invention. Examples 1 to 8 illustrate the preparation of compounds of Formula I, while Examples 9 to 16 illustrate the use of these compounds in the preparation of phenols. Example 17 illustrates the conversion of a phenol into its chlorinated analogue.

EXAMPLE 1

174 g of allyl alcohol was added to a mixture of 298 g of 85% flake potassium hydroxide and 750 ml of sulpholane under nitrogen, and the mixture was heated to 125°–135° C. 272 g of 4-chlorobenzotrifluoride was added over 20 minutes at this temperature. After 2 hours, the reaction mixture was cooled to 30° C., and distillation from the solvent gave 207 g of propenyl 4-trifluoromethylphenyl ether b.p.: 84°–88° C. at 15 Torr.

EXAMPLE 2

A mixture of 116 g of allyl alcohol and 181 g of 4-chlorobenzotrifluoride was added over 1 hour to a mixture of 500 ml of dimethyl sulphoxide and 199 g of 85% flake potassium hydroxide at 90°–105° C. under nitrogen. The mixture was then stirred at this temperature for 3 hours after which time the temperature was reduced to 30° C., the reaction mixture was diluted with 1 liter of water and 750 ml of 60°–80° petrol. The organic phase was separated, and the solvent removed under reduced pressure. The resulting crude product weighed 204 g and was shown by GLC to contain 77% of propenyl 4-trifluoromethylphenyl ether.

EXAMPLE 3

A mixture of 58 g of allyl alcohol and 91 g of 4-chlorobenzotrifluoride was added over 2 hours to a gently refluxing (67° C.) mixture of 250 ml of dimethylsulphoxide, 55 ml 60°–80° petrol and 99.5 g of 85% flake potassium hydroxide. The mixture was then refluxed for a further 21 hours. After work-up as described above, 107.5 g of crude product, containing 91% of the desired product, was obtained. 95 g of pure propenyl 4-trifluoromethylphenyl ether, b.p.: 90°–95° C. at 18 Torr, was isolated by distillation, corresponding to a yield of 86%.

EXAMPLE 4

The procedure of the preceding example was repeated except that the solvent was replaced by 250 ml of sulpholane, 30 ml of 60°–80° petrol and 25 ml of 80°–100° petrol. An 80% yield of pure propenyl 4-trifluoromethylphenyl ether was obtained.

EXAMPLE 5

A mixture of 5.8 g of allyl alcohol, 9.03 g of 4-chlorobenzotrifluoride and 9.9 g of 85% flake potassium hydroxide in 25 ml of diglyme was stirred vigorously under nitrogen for 2 hours at 120° C. followed by 1 hour at 150° C. Analysis by gas chromatography showed the presence of 76% propenyl 4-trifluoromethylphenyl ether.

EXAMPLE 6

A mixture of 53.75 g of 3,4-dichlorobenzotrifluoride, 43.5 g of allyl alcohol and 84.2 g of 85% pellet potassium hydroxide in 375 ml of dimethylsulphoxide was stirred at 80° C. for 2 hours. The mixture was then poured in to 1100 ml of water and extracted with 40/60° petrol. The main product was shown by gas chromatography to be propenyl 2-chloro-4-trifluoromethylphenyl ether.

EXAMPLE 7

A mixture of 50.48 g of methallyl alcohol, 63.2 g of 4-chlorobenzotrifluoride and 69 g of 85% flake potassium hydroxide in 175 ml sulpholane was stirred under nitrogen at 120°–145° C. for 21 hours. The mixture was then cooled, added to 200 ml water and extracted twice with 60°/80° petroleum ether. The solvent was removed and the residue was purified by fractionation to give isobutenyl 4-trifluoromethylphenyl ether, b.p.: 77°–77.5° C. at 8 Torr.

EXAMPLE 8

A mixture of 4.0 kg of allyl alcohol and 6.2 kg of 4-chlorobenzotrifluoride was added over 6 hours to a stirred mixture of 6.8 kg of 85% potassium hydroxide and 17.4 g of tetraglyme at 80° C. The temperature was then raised to 100° C. for 2.5 hours, after which time the reaction mixture was cooled and distilled, and the residue was triturated with toluene and re-distilled to give 4.7 kg of propenyl 4-trifluoromethylphenyl ether.

EXAMPLE 9

A mixture of 60.0 g of propenyl 4-trifluoromethylphenyl ether, 350 ml of methanol and aqueous sulphuric acid (20 ml 98% $H_2SO_4$ in 50 ml water) was refluxed for 4 hours. After dilution with 1200 ml water, the product was extracted twice with toluene. Removal of solvent and distillation of the residue gave 33.43 g of 4-trifluoromethylphenol, b.p.: 63°–64° C. at 6 Torr.

EXAMPLE 10

The procedure of Example 9 was repeated except that the methanol and sulphuric acid were replaced by dimethoxyethane and hydrochloric acid. A similar result was obtained.

EXAMPLE 11

The procedure of Example 10 was repeated except that the dimethoxyethane was replaced by acetone. A similar result was obtained.

EXAMPLE 12

A mixture of 4.04 g of propenyl 4-trifluoromethylphenyl ether, 20 mmol of D-glucose, 200 mg of p-toluenesulphonic acid and 20 ml of carbon tetrachloride was refluxed with stirring under nitrogen for 2.5 hours. Analysis by gas chromatography showed complete conversion to the corresponding phenol.

EXAMPLE 13

The procedure of Example 12 was repeated except that the D-glucose was replaced by D-galactose. A similar result was obtained.

EXAMPLE 14

The procedure of Example 9 was repeated except that the propenyl ether was replaced by the corresponding isobutenyl ether. After 27 hours under reflux, gas chromatographic analysis showed that hydrolysis was 58% complete.

EXAMPLE 15

A mixture of 10.8 g of isobutenyl 4-trifluoromethylphenyl ether, 3.1 g of pentaerythritol, 55 ml of carbon tetrachloride and 0.5 g of p-toluenesulphonic acid was refluxed for 1 hour, after which time gas chromatographic analysis showed that conversion to the phenol was complete.

EXAMPLE 16

A mixture of 0.5 mol of propenyl 4-trifluoromethylphenyl ether, 0.25 mol of pentaerythritol and 5 g of p-toluenesulphonic acid in 500 ml of carbon tetrachloride was stirred and refluxed under nitrogen for 40 minutes. The resulting solution was washed with 250 ml of water, and then dried by azeotroping 150 ml solvent in vacuo. After addition of 150 ml of fresh carbon tetrachloride, chlorine was passed into the solution for 2 hours, after which the solution was washed with 250 ml of water and the solvent was evaporated. The remaining product was purified by fractional distillation to give 74.8 g of 2chloro-4-trifluoromethylphenol, b.p: 52°–53.5° C. at 6 Torr., which was identified and shown by gas chromatography to have a purity of greater than 97%.

EXAMPLE 17

32.4 g of 4-trifluoromethyl phenol was dissolved in 150 ml of carbon tetrachloride and chlorine gas was bubbled into the stirred mixture for 1.25 hours, the temperature being maintained at 20°–30° C. The solvent was then removed in vacuo, and 2-chloro-4-trifluoromethylphenol, b.p.: 64°–66° C. at 10 Torr., was obtained by distillation, in a yield of 93%.

We claim:

1. A compound of the formula

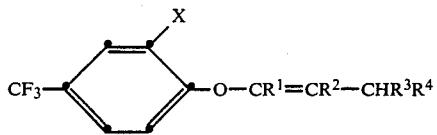

in which X is hydrogen or chlorine, and each of $R^1$, $R^2$, $R^3$ and $R^4$ independently is hydrogen, methyl or ethyl.

2. A compound as claimed in claim 1, in which each of X, $R^1$, $R^2$, $R^3$ and $R^4$ is hydrogen.

3. A process for the preparation of a compound of claim 1, which comprises treating a compound of the formula

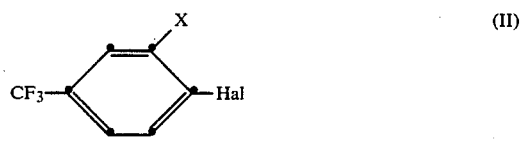

in which Hal is chlorine or fluorine, with a compound the general formula $$HO-CHR^1-CR^2=CR^3R^4$$

in the presence of a base.

4. A process as claimed in claim 3, in which the treatment is carried out at a temperature in the range of from 100°–150° C.

5. A process for the preparation of a compound of the formula

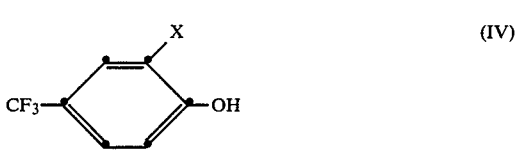

that comprises treating a compound of claim 1 with water or an alcohol under acid conditions.

6. A process as claimed in claim 5, in which X is chlorine, that comprises cleaving a compound of claim 1 in which X is hydrogen, and subsequently chlorinating the resulting compound.

7. A process as claimed in claim 6, in which the cleavage is carried out in the presence of an inert organic solvent, and in the additional presence of a polyfunctional alcohol containing at least two hydroxyl groups, and the resulting compound is chlorinated in situ using elemental chlorine.

* * * * *